United States Patent
Bonney et al.

(10) Patent No.: US 7,552,728 B2
(45) Date of Patent: Jun. 30, 2009

(54) DRUG DELIVERY DEVICE

(75) Inventors: Stanley George Bonney, Ware (GB);
Michael Birsha Davies, Ware (GB);
Paul Kenneth Rand, Ware (GB)

(73) Assignee: Glaxo Group Limited, Greenford, Middlesex (GB)

( * ) Notice: Subject to any disclaimer, the term of this patent is extended or adjusted under 35 U.S.C. 154(b) by 490 days.

(21) Appl. No.: 10/534,383

(22) PCT Filed: Nov. 5, 2003

(86) PCT No.: PCT/EP03/12436

§ 371 (c)(1),
(2), (4) Date: May 3, 2005

(87) PCT Pub. No.: WO2004/041337

PCT Pub. Date: May 21, 2004

(65) Prior Publication Data

US 2006/0084908 A1    Apr. 20, 2006

(30) Foreign Application Priority Data

Nov. 7, 2002    (GB)    ................................. 0226022.2

(51) Int. Cl.
*A61M 11/00*    (2006.01)
*A61M 11/06*    (2006.01)
*A61M 11/08*    (2006.01)

(52) U.S. Cl. ............................ 128/200.14; 128/200.17; 128/200.23; 128/203.12; 128/207.14; 128/207.18; 222/173; 222/182; 222/183

(58) Field of Classification Search ............ 128/200.11, 128/200.12, 200.14, 200.18, 200.21, 200.23, 128/200.24, 200.27, 200.22
See application file for complete search history.

(56) References Cited

U.S. PATENT DOCUMENTS

| 3,865,279 A | | 2/1975 | James |
| 5,069,204 A | * | 12/1991 | Smith et al. ............. 128/200.23 |
| 5,482,030 A | | 1/1996 | Klein |
| 5,826,571 A | * | 10/1998 | Casper et al. .......... 128/200.23 |
| 6,273,084 B1 | * | 8/2001 | Frid ....................... 128/200.23 |
| 2002/0047021 A1 | | 4/2002 | Blacker et al. |
| 2002/0056449 A1 | * | 5/2002 | Wakefield et al. ...... 128/200.23 |

FOREIGN PATENT DOCUMENTS

| EP | 0075548 | | 3/1983 |
| EP | 0414536 | | 2/1991 |
| EP | 0428380 | | 5/1991 |
| GB | 2196262 A | | 4/1988 |
| WO | WO 9856444 A1 | * | 12/1998 |

* cited by examiner

*Primary Examiner*—Justine R Yu
*Assistant Examiner*—Clinton Ostrup
(74) *Attorney, Agent, or Firm*—Dwight S. Walker

(57) ABSTRACT

A drug delivery device for delivering to a patient a drug composition from a container which contains the drug composition where the container is adapted to be placed in a dispensing mode thereof on application of an actuating condition thereto is disclosed. The device includes a dispensing unit adapted to receive the container, the dispensing unit having an actuating mechanism operable to apply the actuating condition to the container and an outlet through which the drug composition is dispensable from the device, and a removable casing unit for the dispensing unit. The dispensing and casing units have securing features for releasably, fixedly securing the units together, and the dispensing unit is operable to apply the actuating condition to the container when fixedly secured to the casing unit and when independent from the casing unit.

34 Claims, 15 Drawing Sheets

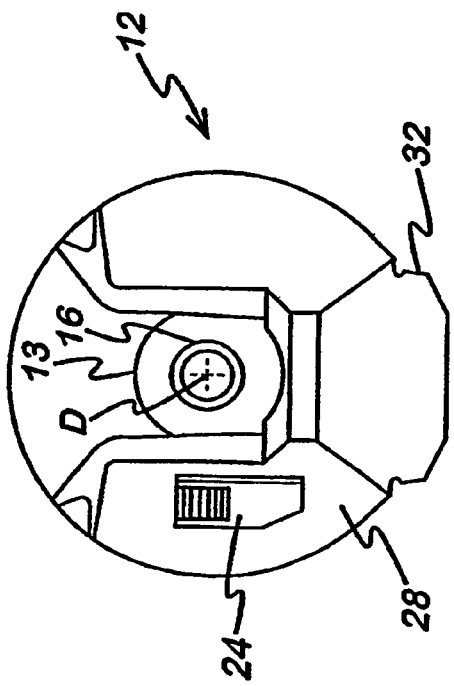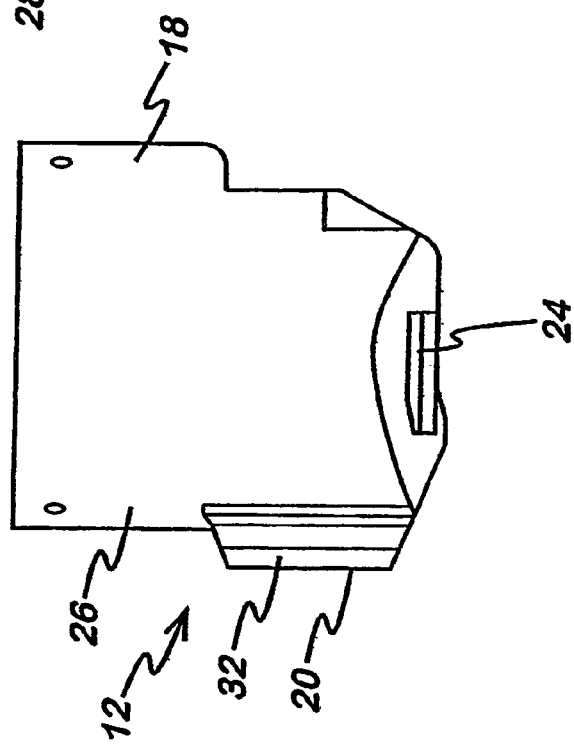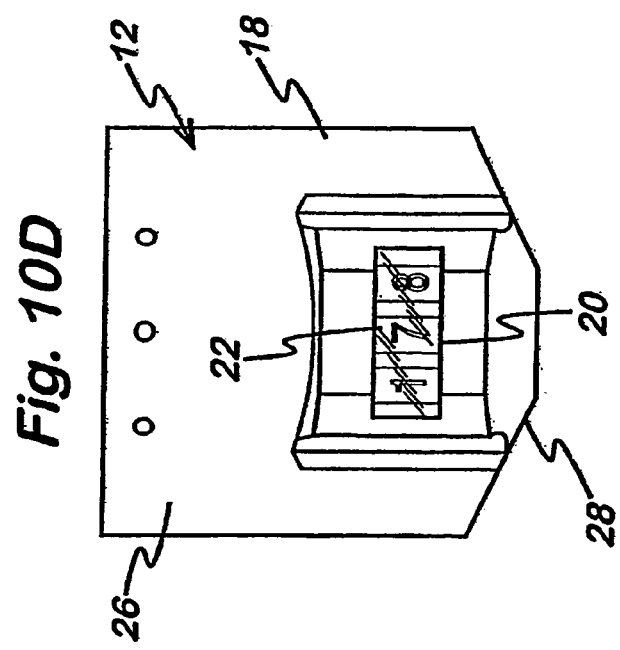

DRUG DELIVERY DEVICE

RELATED APPLICATIONS

This application is filed pursuant to 35 U.S.C. § 371 as a United States National Phase Application of International Patent Application Serial No. PCT/EP2003/012436 filed Nov. 5, 2003, which claims priority from Great Britain Application No. 0226022.2 filed in the United Kingdom on Nov. 7, 2002.

FIELD OF THE INVENTION

The present invention relates to a drug delivery device for delivering to a patient a drug composition from a container which contains the drug composition, the container adapted to be placed in a dispensing mode thereof on application of an actuating condition thereto (hereinafter a "device of the type defined").

BACKGROUND OF THE INVENTION

Before a device of the type defined can be legally marketed, it is first necessary for the device to be approved by the appropriate regulatory authority, e.g. the Food and Drug Administration (FDA) in the United States of America.

The present invention proposes to provide a device of the type defined which can shorten the lead time for it to get to market.

SUMMARY OF THE INVENTION

According to the present invention there is provided a device of the type defined comprising:
  a dispensing unit adapted to receive the container, the dispensing unit having an actuating mechanism operable to apply the actuating condition to the container and an outlet through which the drug composition is dispensable from the device; and
  a removable casing unit for the dispensing unit;

with:
  the dispensing and casing units having securing features for releasably, fixedly securing the units together; and
  the dispensing unit being operable to apply the actuating condition to the container when fixedly secured to the casing unit and when independent from the casing unit.

Preferably, the casing unit is movable between a closed state in which it is able to enclose the dispensing unit with the container received therein, and an open state which enables the actuating mechanism of the dispensing unit to be operated to apply the actuating condition to the container and for the resultant dispensed drug composition to be discharged from the outlet.

The device may be hand-held, for instance the device may be adapted to be held by the casing unit when assembled with the dispensing unit. Preferably, the dispensing unit is adapted to be hand-operated to apply the actuating condition to the container. For example, the device may be adapted so that, when the casing unit is held by a hand of a patient, the hand of the patient is also able to operate the actuating mechanism of the dispensing unit.

Preferably, the actuating condition is movement of a first part of the container relative to a second part and the actuating mechanism of the dispensing unit is able to effect said relative movement. As an example, the actuating mechanism of the dispensing unit is adapted in use to hold the second part of the container stationary and to allow the first part to move relative thereto.

The container may have a plurality of doses of the drug composition and be fitted with a dose counter mechanism, and the dispensing unit has a dose counter advancing mechanism adapted in use to advance the dose counter mechanism when the actuating condition is applied by the dispensing unit to the container. Conveniently, the dose counter advancing mechanism has a mechanical feature which engages the dose counter mechanism to advance it on relative movement of the first part of the container to the second part thereof. The mechanical feature may be a post and/or a part of a rack-and-pinion mechanism, the other part being in the dose counter mechanism.

Ideally, the outlet forms a part of a nozzle arrangement in the dispensing unit for directing the drug composition to the patient on application of the actuating condition to the container.

The second part of the container may present an outlet of the container. In use, the outlet of the container is preferably held stationary by the nozzle arrangement. Preferably, the second part is a valve which is moved between a closed position and an open position on relative movement with the first part. In an embodiment of the invention, such as hereinafter described, the container is an aerosol container with the first part a canister.

According to the invention there is further provided the device of the invention in combination with the container and the drug composition therein. The drug composition may be for the treatment or prophylaxis of a respiratory disease or disorder, e.g. rhinitis.

The device may be an inhalation device or an intranasal device.

According to the invention there is also provided a drug delivery system comprising the device of the invention and at least one further dispensing unit, the dispensing units being interchangeable with one another. So, refill containers could be supplied "ready-for-use" in a replacement dispensing unit.

The present invention also provides a drug delivery system comprising the device of the invention and at least one further casing unit of different appearance to the other casing unit, the casing units being interchangeable with one another. Thus, removing the dispensing unit from one of the casing units and placing it in the other casing unit gives the drug delivery device a new appearance. In other words, the aesthetics, but not the functionality, of the device can be customized to certain patient groups, e.g. based on demographics, nationality etc.

The present invention yet further provides a method of manufacturing a drug delivery device for delivery of a drug formulated in a drug container which is adapted to be placed in a dispensing mode on application of an actuating condition thereto, the method comprising the steps of:
(a) providing a dispensing unit for receiving the container which has an actuating mechanism for applying the actuating condition thereto and an outlet through which the drug formulation is dispensable from the dispenser on application of the actuating condition thereto, and
(b) separately providing a casing unit adapted to fixedly hold the dispensing unit such that the drug is dispensable from the container by the dispensing unit when held by the casing unit.

The invention additionally provides a drug delivery device formed by the method of the invention.

Further preferred features of the invention are set forth in the claims appended hereto.

A non-limiting exemplary embodiment of the invention will now be described with reference to the accompanying FIGURES of drawings.

BRIEF DESCRIPTION OF THE DRAWINGS OF THE EXEMPLARY EMBODIMENT

FIG. 10B is a plan view of the dose counter head.

FIG. 10C is a side view of the dose counter head.

FIG. 10D is a rear view of the dose counter head.

Figure 15A:
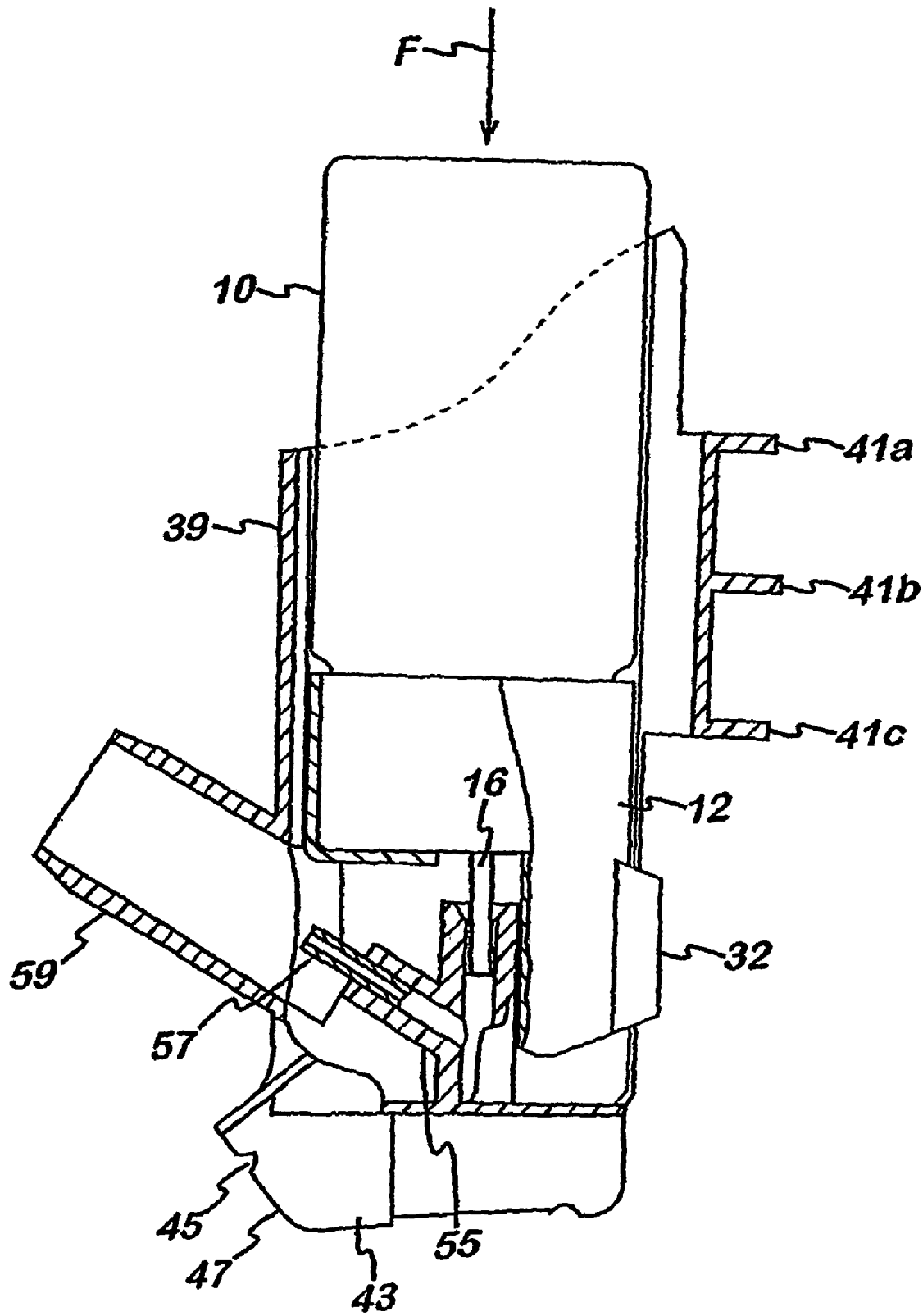
FIG. 15A is a schematic side view, partly in cross section, of the canister unit mounted in the inner actuating part in an inoperative position.
Figure 15B:
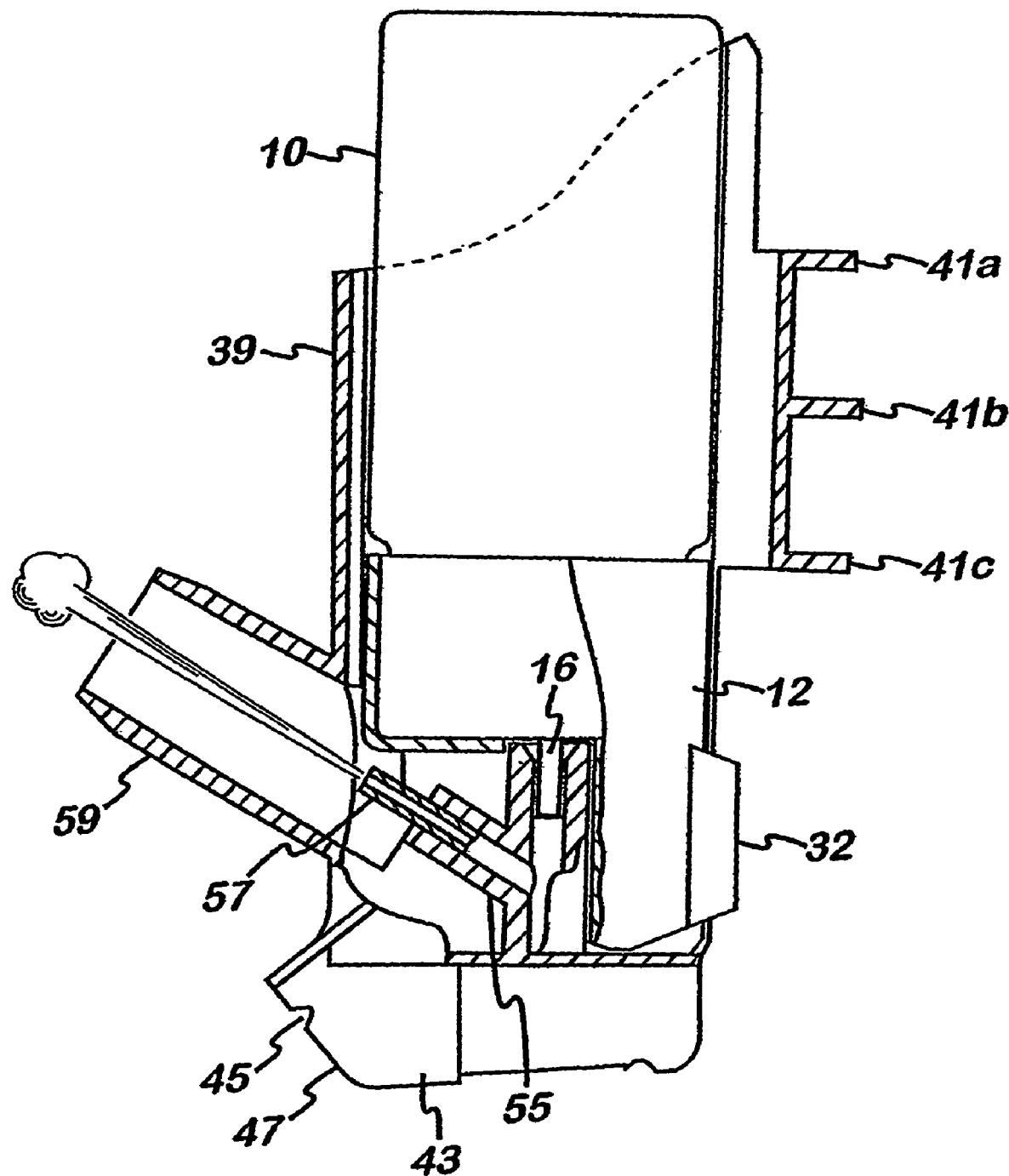

FIG. 15B corresponds to FIG. 15A, but with the canister unit in an operative position relative to the inner actuating part.

DETAILED DESCRIPTION OF THE EXEMPLARY EMBODIMENT

Figure 1:
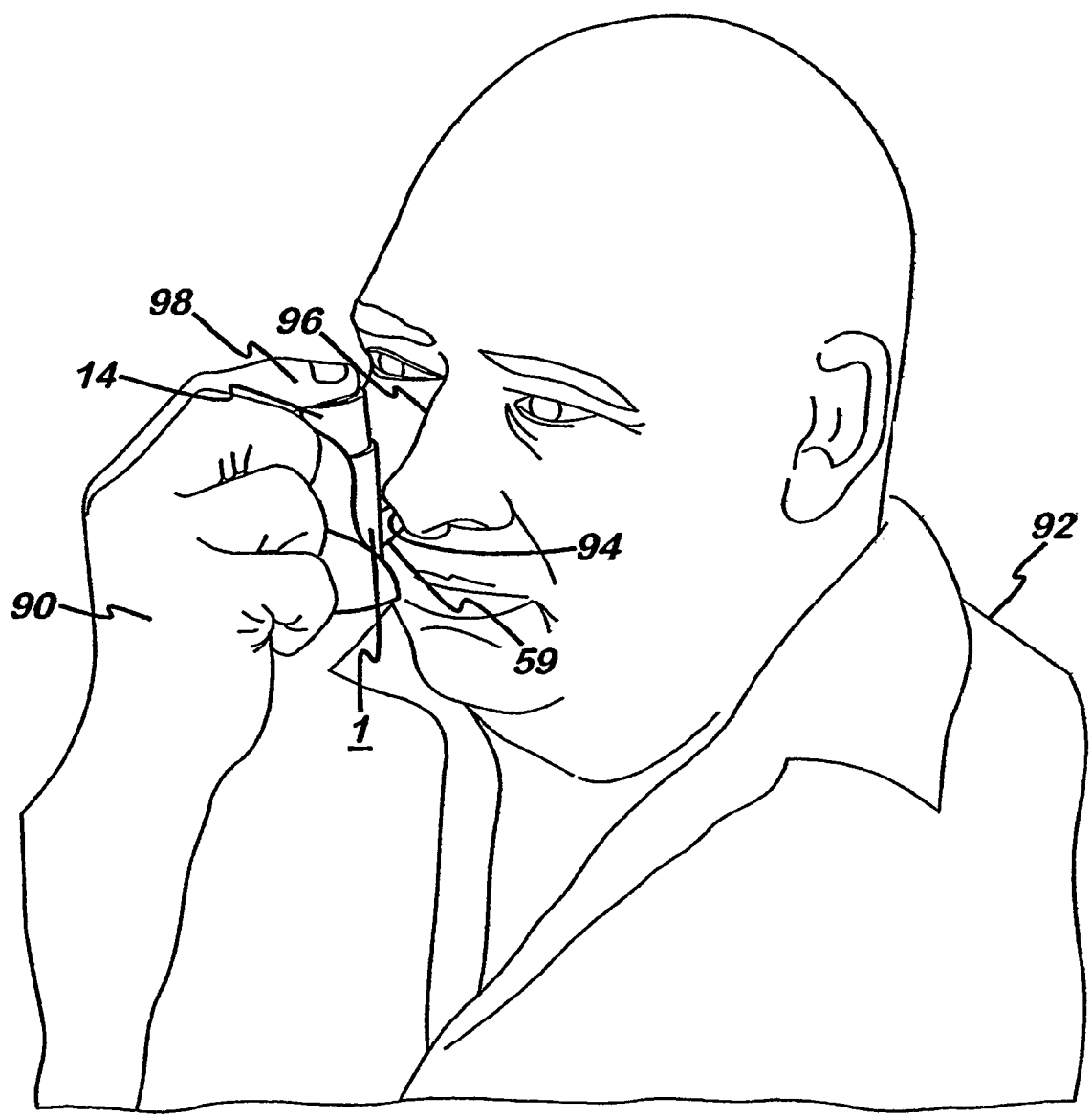
FIG. 1 is a schematic view of a patient using an intranasal device in accordance with the invention.

In the FIGURES of drawings there is shown a drug delivery device 1 in accordance with the present invention, the device 1 in this particular non-limiting embodiment being an intranasal drug delivery device, as shown graphically in FIG. 1.

Figure 6:
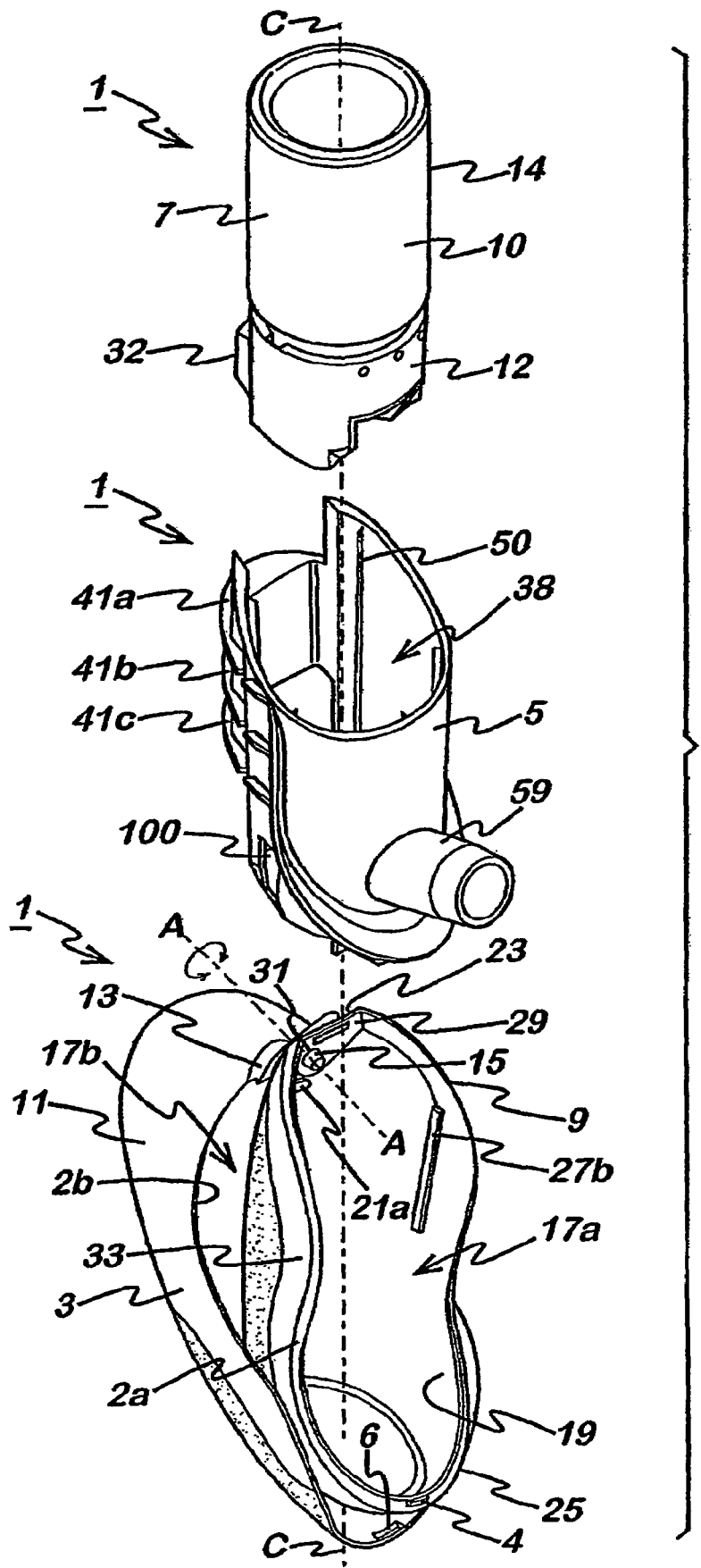
FIG. 6 is an exploded perspective view of the intranasal device with the outer casing part in its nested state.

As best shown in FIG. 6, the intranasal drug delivery device 1 comprises as component parts the following:
- an outer casing part 3;
- a one-piece inner actuating part 5 which is releasably securable in the outer casing part 3; and
- a canister unit 7 releasably securable in the inner actuating part 5.

Outer Casing Part

Referring to FIGS. 2 to 7, the outer casing part 3 of the intranasal device 1 is formed from two shell-like members, namely a container member 9 and a cover member 11, which are connected to one another through a hinge 13. The container and cover members 9, 11 each respectively present a cavity 17a; 17b having a mouth bound by a lip surface 2a; 2b (FIG. 6).

Both the container member 9 and the cover member 11 are formed from a plastics material by injection moulding, although other types of moulding processes can, of course, be used. The container and cover members 9, 11 are preferably both formed from polypropylene with the container member 11 being opaque, but with the cover member 11 being transparent or semi-transparent. Other plastics material combinations are possible, although it is preferable for the cover member 11 to be transparent/semi-transparent for reasons which will become apparent hereinafter.

Figure 7:
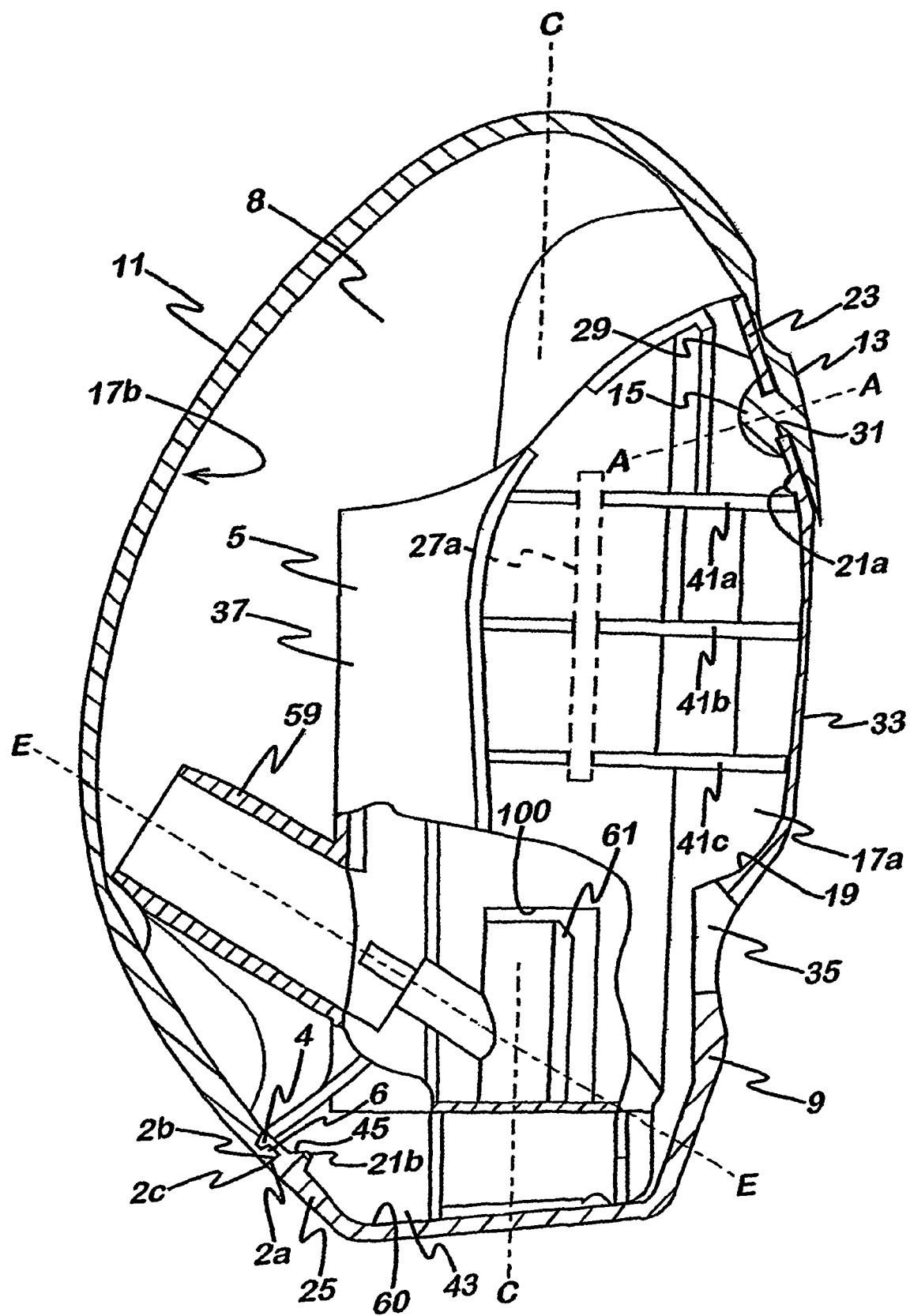
FIG. 7 is a schematic, partial sectional side view of an inner actuating part of the intranasal device mounted in the outer casing part.

As shown in FIG. 7, for example, the cover member 11 is integrally formed with the hinge 13, colloquially known as a "living hinge", and the hinge 13 includes a knob 15.

Turning to FIGS. 6 and 7, on an inner surface 19 of the cavity 17a of the shell-like container member 9 there is formed a pair of protrusions or ribs 21a, 21b to co-operate with complementary surfaces of the inner actuating part 5 to form a snap-fit connection between the outer casing part 3 and the inner actuating part 5, as will also be discussed in more detail hereinafter. A first one of the ribs 21a is disposed towards an upper end 23 of the container member 9, whereas the other rib 21b is disposed towards a lower end 25 of the container member 9.

Also formed on the inner surface 19 of the cavity 17a of the container member 9 are longitudinally extending ribs 27a, 27b. The longitudinal ribs 27a, 27b are disposed on opposing sides of the container member 9 and act as anti-rotational retainers on the inner actuating part 5 in the cavity 17a.

At the upper end 23 of the container member 9 there is formed a bevel 29 through which an aperture 31 extends from an outer surface 33 of the container member 9 to the inner surface 19 of the cavity 17a. From FIG. 7 it will be seen that the aperture 31 is adapted to receive the knob 15 on the hinge 13. Although the diameter of the knob 15 is greater than the diameter of the aperture 31, the knob 15 is able to be pushed through the aperture 31 for capture therein due to the container and cover members 9, 11 being sufficiently resiliently deformable due to their shell-like nature and the materials used. Moreover, the knob 15 is able to be withdrawn from the aperture 31 upon application of a sufficient pulling force thereto for separation of the container and cover members 9, 11.

Figure 2:
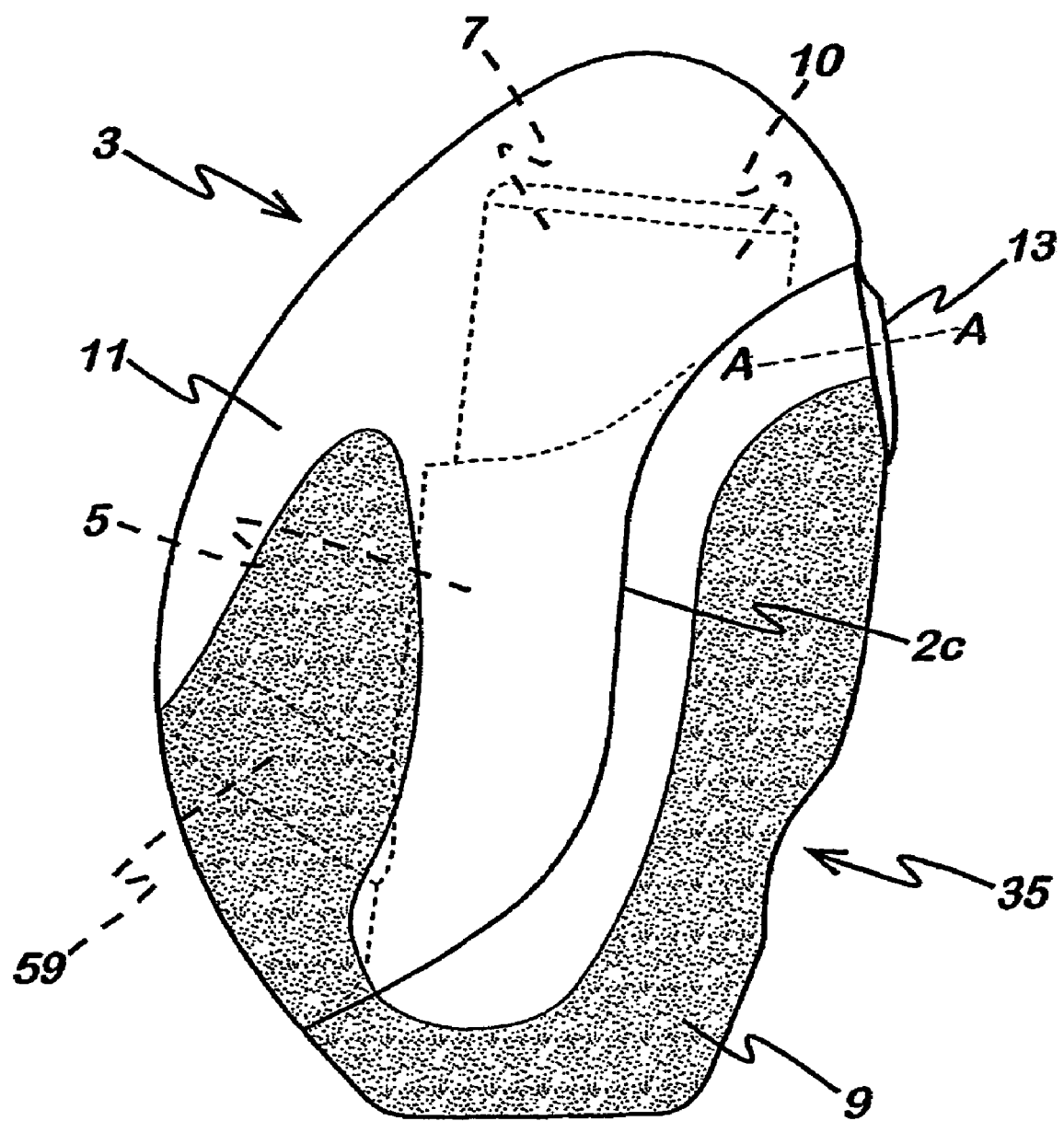
FIG. 2 is a side view of the intranasal device showing an outer casing part thereof comprising cover and container members and a hinge therebetween, the outer casing part in a closed state to protect inner parts of the device.
Figure 3:
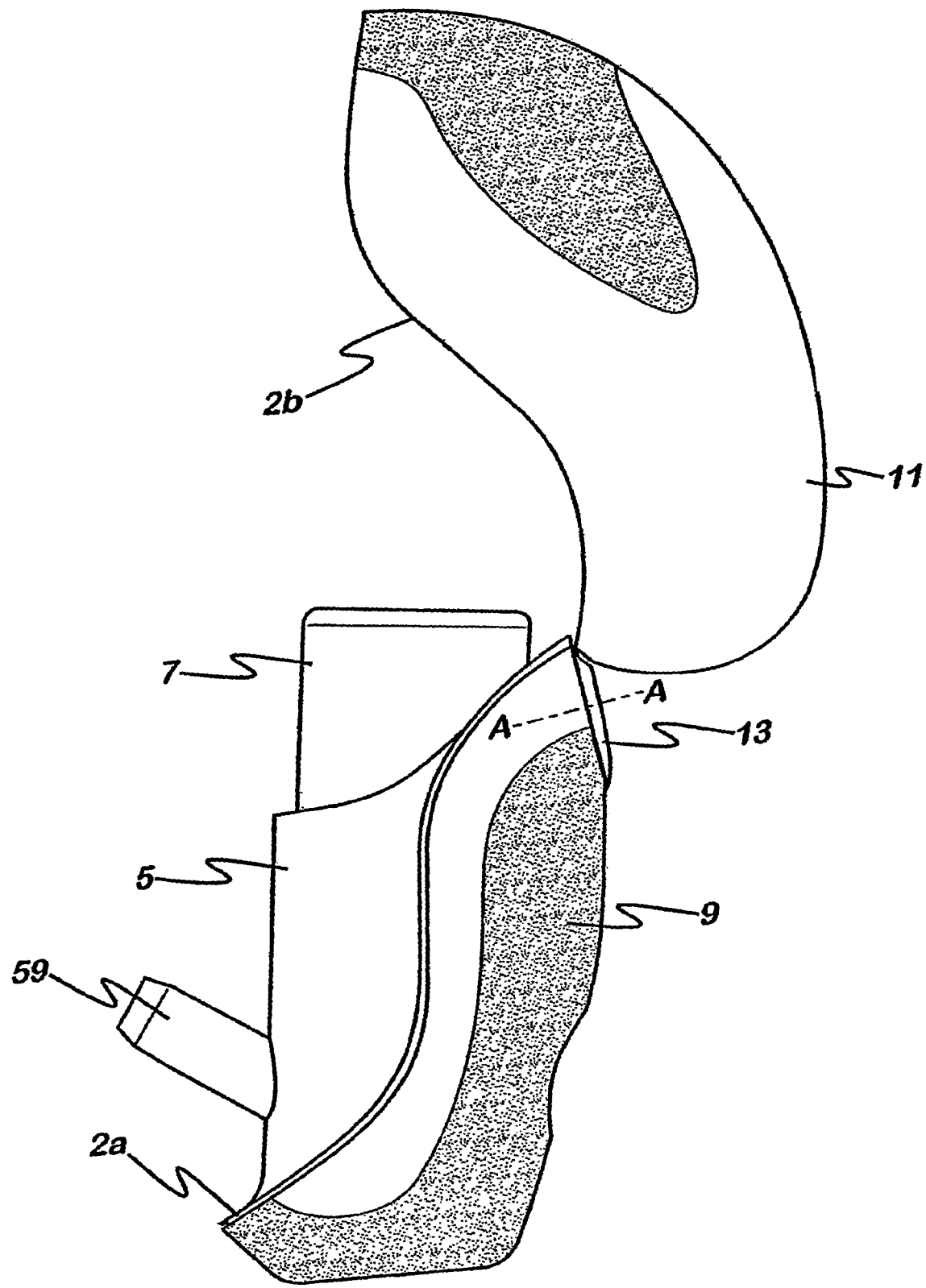
FIG. 3 is a side view of the intranasal device with the outer casing part hinged to an open state to allow access to the inner parts.
Figure 5:
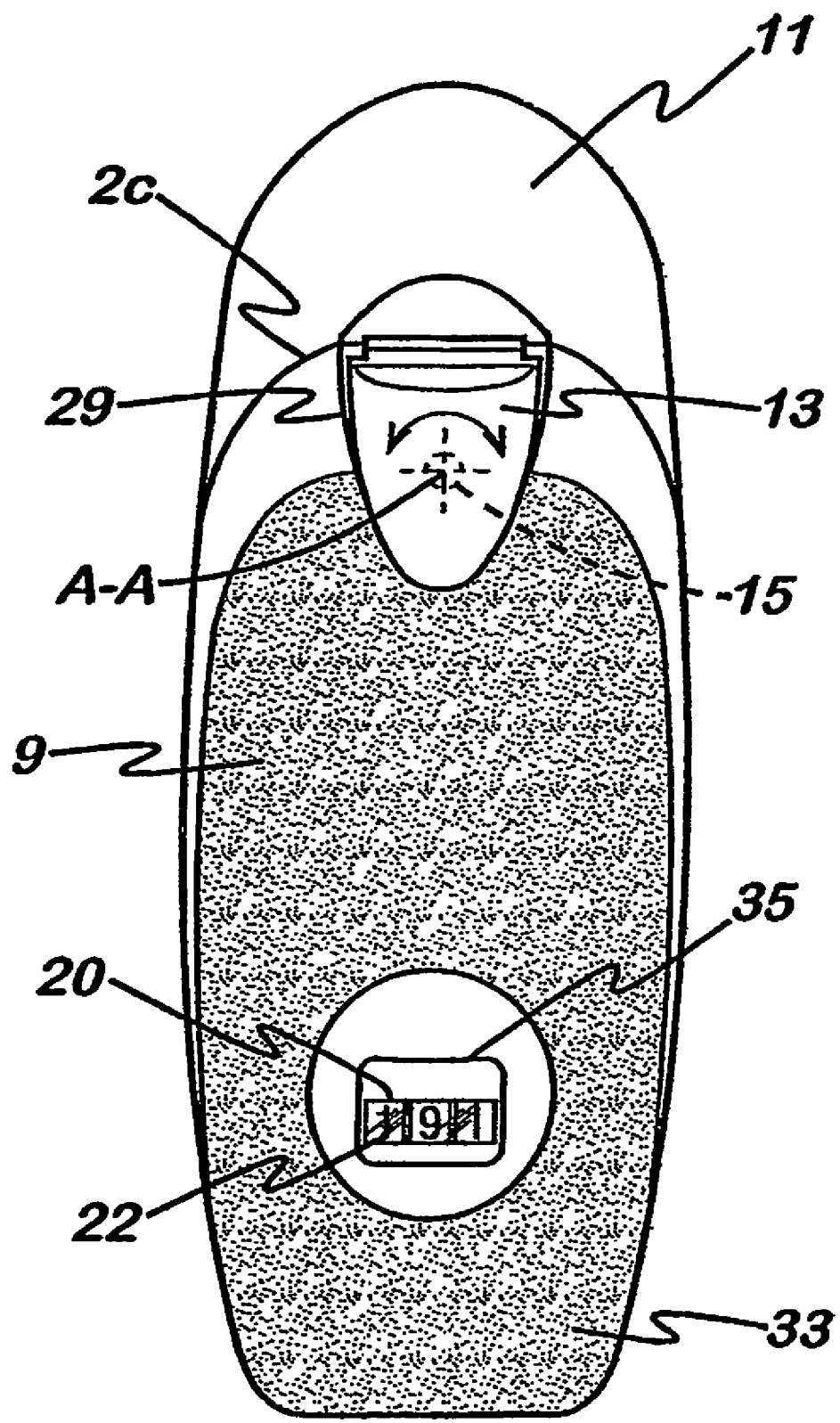
FIG. 5 is a rear view of the device with the outer casing part in its closed state.

As shown in FIGS. 2 to 5, the mounting of the knob 15 of the hinge 13 in the aperture 31 of the container member 9 enables two degrees of movement of the cover member 11 on the container member 9 as follows:

(1) Hinging of the cover member 11 from a closed position shown in FIGS. 2 and 5, in which the respective lip surfaces 2a, 2b of the cavities 17a, 17b of the container and cover members 9, 11 abut one another at an interface 2c to form an enclosed internal space 8 (see FIG. 7), to an open position shown in FIG. 3, in which the cavity 17a of the container member 9 is accessible. As will be understood from FIGS. 6 and 7, the lip surfaces 2a, 2b are each provided with detent elements 4, 6 which engage with one another in the closed position to provide a releasable snap-fit fastening of the container and cover members 9, 11 in the closed position.

Figure 4A:
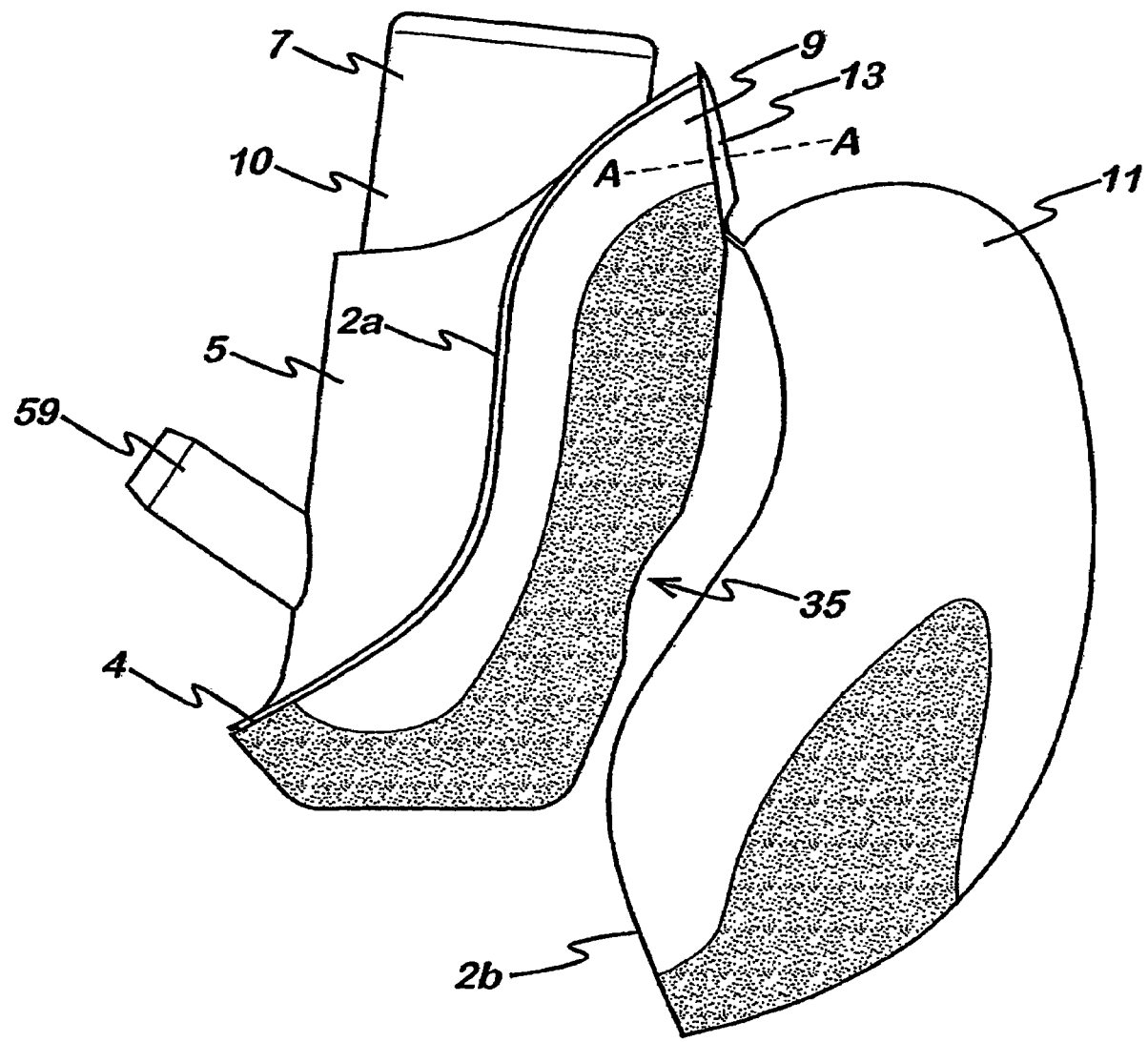
FIG. 4A is a side view of the intranasal device in its open state with the cover member pivoted behind the container member FIG. 4B corresponds to FIG. 4A, but with the container and cover members nested.

(2) Rotary or pivotable movement of the cover member 11 about the aperture 31 (pivot axis A-A) from a first angular position corresponding to the open position shown in FIG. 3 to a second angular position shown in FIG. 4A in which the cover member 11 is located behind the container member 9. The cover member 11 is not able to be pivoted about the pivot axis A-A from its closed position due to the interengagement of the lip surfaces 2a, 2b.

Figure 4B:
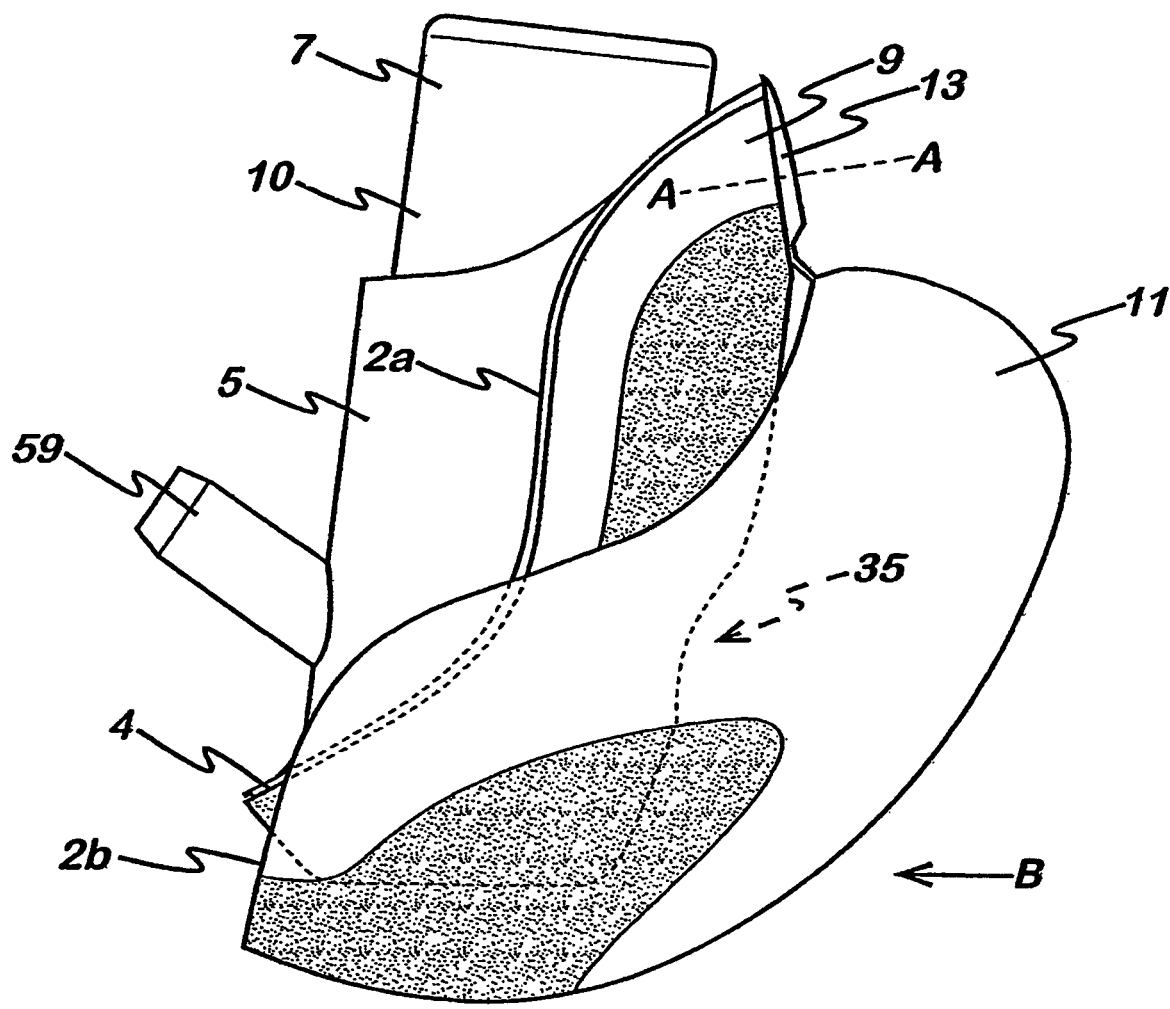

As shown in FIG. 4B, when the cover member 11 is in the second angular position it is able to nest with the container member 9 by forward movement in the direction of arrow B. In other words, the concave cavity 17b of the shell-like cover member 11 is able to slidingly receive the convex rear surface of the container member 9. In the nesting position, an interference fit is formed between the container and cover members 9, 11 to releasable fasten them in the nesting position.

When the container and cover members 9,11 adopt the nesting configuration, an ergonomic unit is formed which is able to be easily, and comfortably, held by a hand 90 of a patient 92, as shown in FIG. 1. In this mode, the outer casing part 3 is able to act as a holder or applicator of the drug delivery device 1.

As shown in FIG. 5, for example, the outer surface 33 at the rear side of the container member 9 is provided with a window 35. As will be understood from FIGS. 4A and 4B, the window 35 is covered by the cover member 11 when in its second angular position. If the cover member 11 is transparent or semi-transparent, the window 35 is then visible through the cover member 11 when in its second angular position.

If need be, an indexing or detent mechanism could be provided for indexing the cover member 11 in one or more predetermined angular positions about the pivot axis A-A, for instance the first and/or second angular positions and/or angular positions therebetween. The user would then have a tactile feedback indicating that the cover member 11 is in the correct angular position, e.g. for nesting with the container member 9. One way of achieving the indexing mechanism would be a male-and-female arrangement in which male (or female) surface features are formed in the outer surface 33 of the container member 9 at the required angular dispositions about the pivot axis A-A and one or more complementary female (or male) surface features are correspondingly arranged on the inner surface of the hinge 13 about the knob 15. When the male feature is located in the, or one of the, female features (or vice-versa), the cover member 11 is indexed in a predetermined angular position. To move the cover member 11 to a new angular position, rotation of the cover member 11 about the pivot axis A-A causes disconnection of the first indexing connection until the male and female features re-engage at a new angular position of the cover member 11

Figure 8:
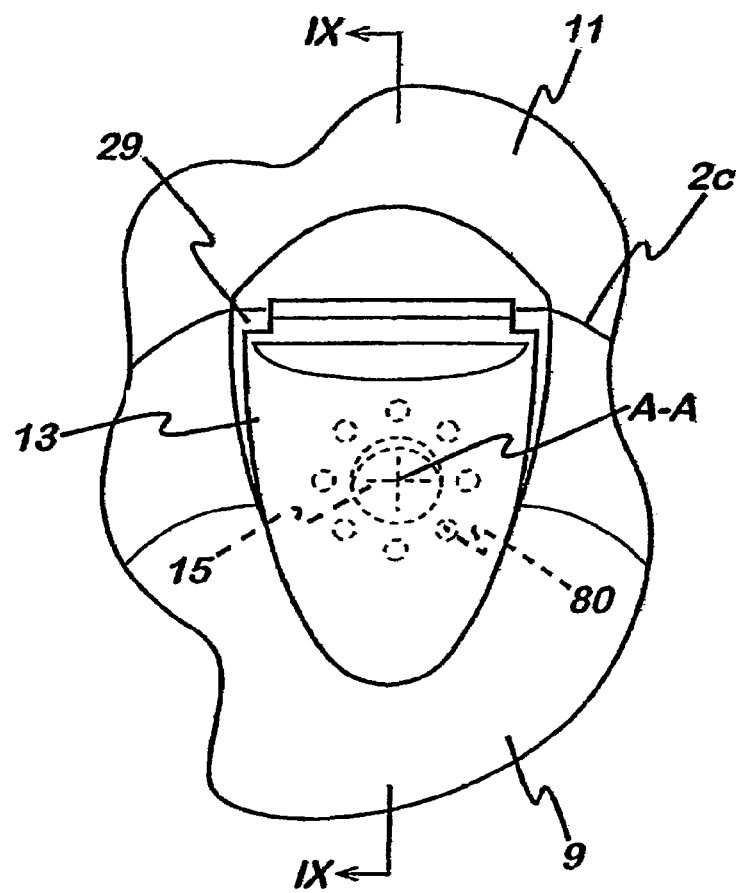
FIG. 8 is a enlarged fragmentary view of an alternative hinge construction for the outer casing part.
Figure 9:
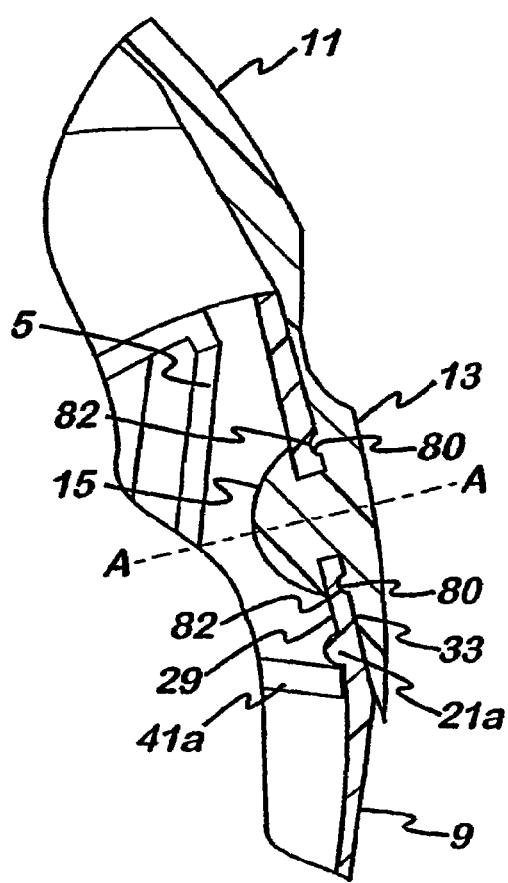
FIG. 9 is a cross-sectional side view of the alternative hinge construction along line IX-IX in FIG. 8.

By way of example, a "ball-and-socket" indexing mechanism is shown in FIGS. 8 and 9 in which a circular array of protrusions 80 is formed on the inner surface of the hinge 13 co-axially with the knob 15, and a complementary circular array of sockets 82 is formed in the outer surface 33 of the bevel 29 on the container member 9 co-axially with the pivot axis A-A. When the protrusions 80 are located in the complementary sockets 82, the cover member 11 is indexed in one of a plurality of different predetermined angular positions it can adopt about the pivot axis A-A, for instance the first angular position of FIGS. 2 and 3 or the second angular position of FIGS. 4A and 4B. The cover member 11 is then able to be indexed in a new predetermined angular position by pivoting it about the pivot axis A-A to disconnect and re-engage the protrusions 80 and sockets 82, e.g. from the first angular position to the second angular position and vice-versa.

In an alternative embodiment, an indexing mechanism may be provided which indexes the cover member 11 in an end angular position between the first and second angular positions mentioned previously such that the cover member 11 does not cover the window 35 in the container member 9, thereby allowing the window 35 to be viewed by a user of the intranasal device 1.

Canister Unit

Turning attention now to FIGS. 10A to 10D, the canister unit 7 comprises an aerosol canister 10 of standard type which contains a drug formulated in a fluid propellant, e.g. a liquefied gas propellant such as a hydrofluoro alkane (HFA), for instance 1,1,1,2-tetrafluoroethane ($CF_3CH_2F$) (known as "HFA 134a") or 1,1,1,2,3,3,3-heptafluoro-n-propane ($CF_3CHFCF_3$) (known as "HFA 227") or a mixture thereof. The drug is typically for the treatment or prophylaxis of respiratory diseases or disorders, for example rhinitis. The drug may also be for the treatment or prophylaxis of other types of disease or disorder through systemic action of the drug. The canister unit 7 further comprises a dose counter head 12.

The canister 10 has a metal canister body 14 which, as known in the art, e.g. from metered dose inhalers (MDIs), has an open end which is capped by a valve assembly including a valve stem 16 which is mounted so it is movable relative to the canister body 14, between a retracted or open position relative to the canister body 14 in which the drug formulation is discharged from the canister 10 through the valve stem 16, and an extended or closed position relative to the canister body 14 in which the drug formulation is prevented from being discharged from the canister 10.

As known in the art, the valve assembly includes a biasing mechanism such as a spring (not shown) for biasing the valve stem 16 to the closed position. The valve assembly may be such as to further include a metering mechanism which operates so that a metered dose of the drug formulation is discharged when the valve stem 16 is in its open position. Typically, the valve assembly will have a metering chamber of fixed volume which in the closed position of the valve stem 16 is sealed from the external environment but in fluid communication with the canister body 14 whereby the metering chamber is filled with the drug formulation, and which in the open position of the valve stem is sealed from the canister body 14 and its contents, but placed in fluid communication with the external environment so that the metered dose of the drug formulation in the chamber is discharged to the external environment through the valve stem 16.

In this embodiment of the invention the valve assembly is a metering valve which dispenses a metered dose of the drug formulation per actuation thereof. A suitable metering valve is disclosed in WO98/29321, the content of which is hereby incorporated herein by reference.

The dose counter head 12 of the canister unit 7 has a hollow plastics body 18 of a plastics material which is fixedly secured to the canister 10 over the outlet end of the canister 10 having the valve assembly. The dose counter body 18 is fixed to the canister 10 to prevent it being taken off the canister 10, although it is free to rotate about a longitudinal axis D-D of the canister unit 7. The dose counter body 18 may be fixed to the canister 10 in the manner described and shown in WO01/28887 (Glaxo/Brand et al), the content of which is hereby incorporated herein by reference.

As best shown in FIG. 10D, the dose counter body 18 is formed with a display window 20. The dose counter head 12 further includes a dose counting mechanism (not shown) in the body 18 which, when actuated, advances a counter 22 thereof located in the window 20. When the counter 22 is advanced it results in the dose count shown thereby in the window 20 either being incremented to indicate the number of doses dispensed or, more preferably, decremented to show the number of doses left in the canister 10. The dose counter mechanism can take one of the forms described and shown in WO98/56444 (Glaxo/Rand et al) or Applicant's co-pending International patent application No. PCT/EP03/06466 (Applicant's Ref: PB60210), the contents of which are incorporated herein by reference.

An aperture 24 is provided in the outer surface of the dose counter body 18 to enable a driver to engage with the dose counting mechanism to advance the counter 22 when a dose of the drug formulation is dispensed from the canister 10 by the inner actuating part 5, as will be described in more detail hereinafter.

Figure 10A:
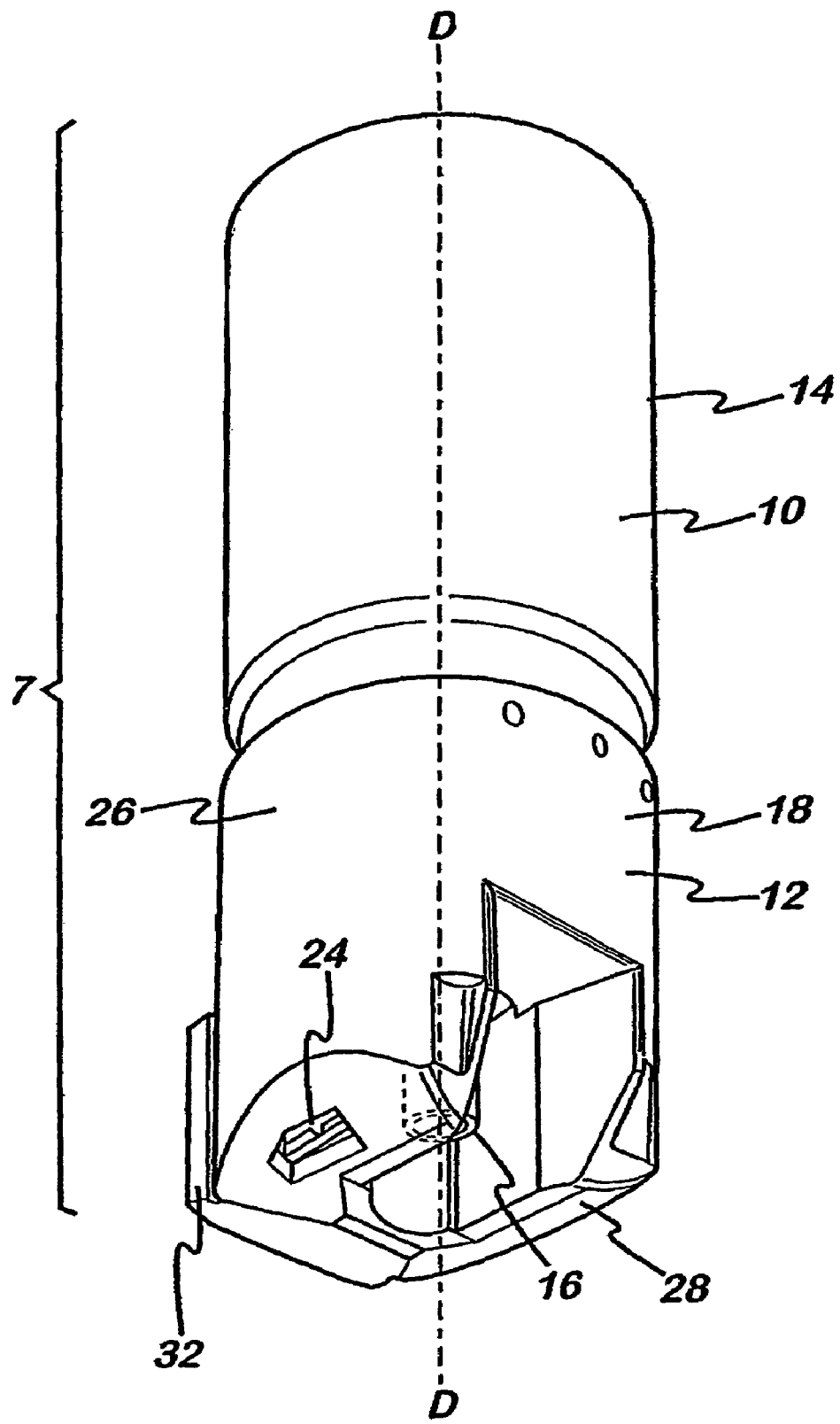
FIG. 10A is a perspective view of a canister unit of the intranasal device comprising a canister and a dose counter head mounted on the canister.

As shown in FIGS. 10A and 10B, the dose counter body 18 comprises a skirt-like lower section 26 and a U-shaped upper section 28. The dose counter body 18 also has a central opening 13 to the U-shaped upper section 28 through which the valve stem 16 protrudes. It will further be seen from FIGS. 10C and 10D that the dose counter window 20 is formed in a protrusion 32 in the outer peripheral surface of the U-shaped upper section 28.

Inner Actuating Part

Attention is now turned to FIGS. 11 to 15B which show the inner actuating part 5. The inner actuating part 5 is of a plastics material, preferably polypropylene, made by a moulding process, preferably by injection moulding.

As will be seen, the inner actuating part 5 is of tubular construction having a main body 37 defining an axially-oriented cavity 38. The main body 37 has an outer surface 39 having a rear section 40 of shape and size which is complementary to the shape and size of the inner surface 19 of the container member cavity 17a, thereby enabling the inner actuating part 5 to fit snugly in the container member cavity 17a, as shown in FIGS. 3 and 7, for example. More particularly, the rear section 40 of the main body outer surface 39 is provided with a series of axially-spaced, circumferential ribs 41a-c which act as spacers to position the inner actuating part 5 along a vertical axis C-C in the container member 9, as shown in FIGS. 6 and 7. Moreover, as further shown in FIG. 7, the uppermost circumferential rib 41a is adapted to be snap fit underneath the locking rib 21a on the inner surface 19 of the container member 9.

Figure 12:
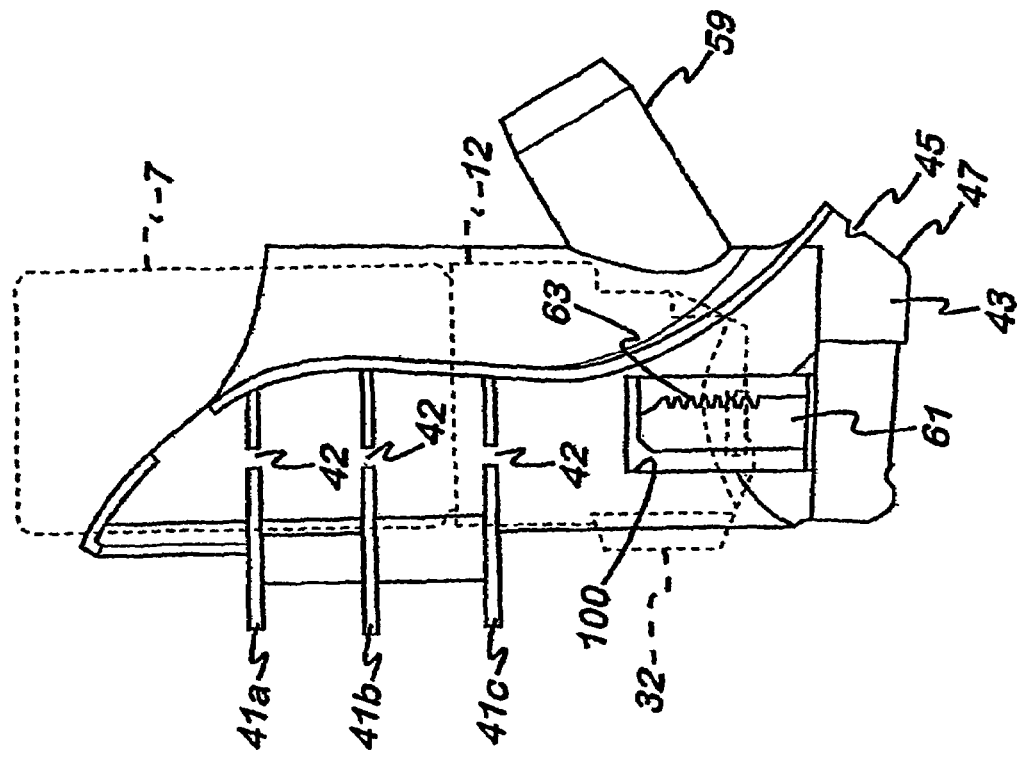
FIG. 12 is an opposite side view of the inner actuating part with the canister unit shown mounted therein in ghost.
Figure 11:
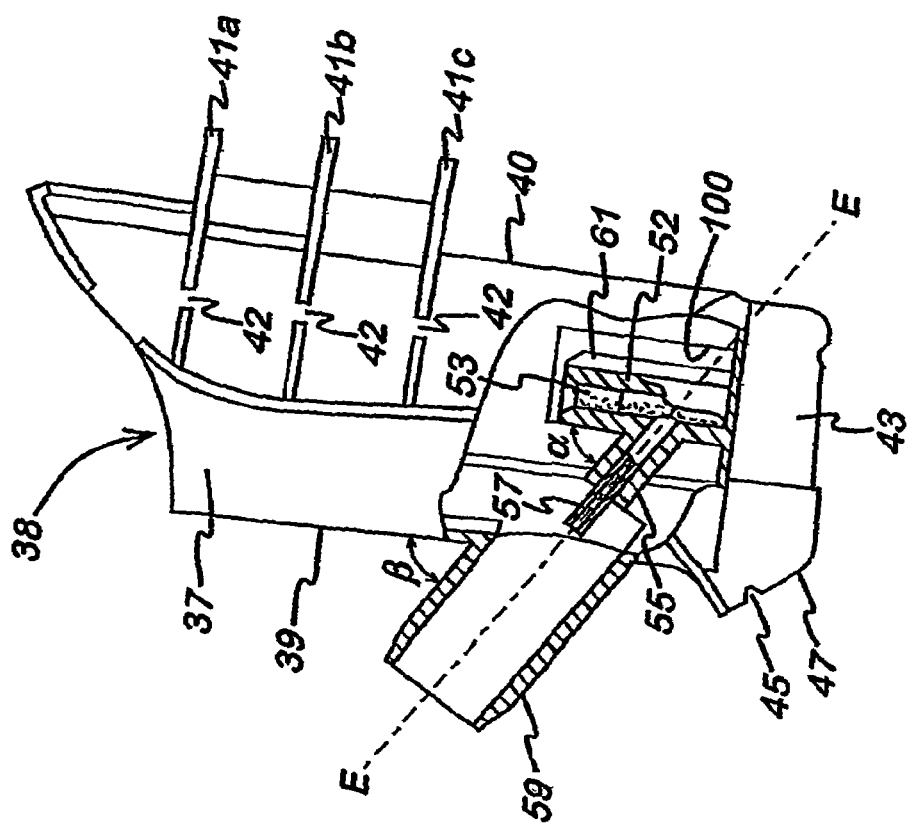
FIG. 11 is schematic side view, partly in section, of the inner actuating part of the intranasal device.
Figure 13:
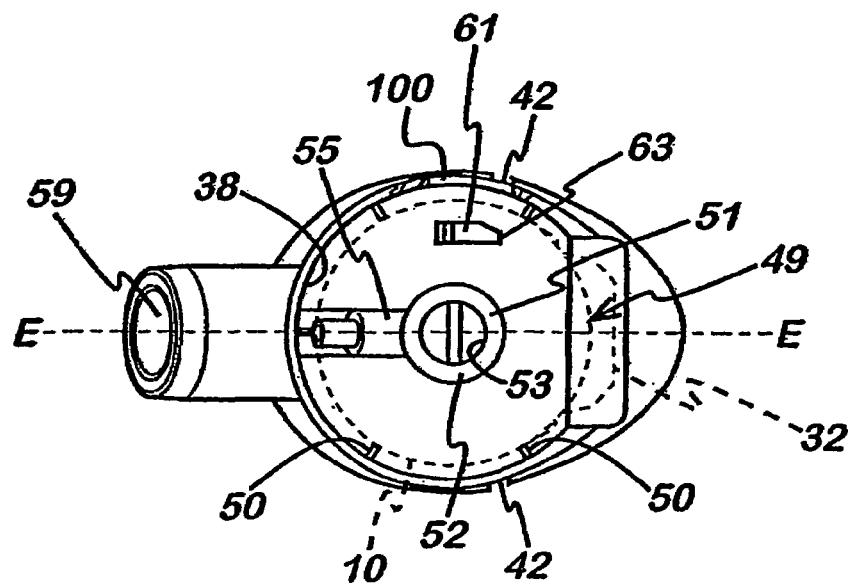
FIG. 13 is a plan view of the inner actuating part.
Figure 14:
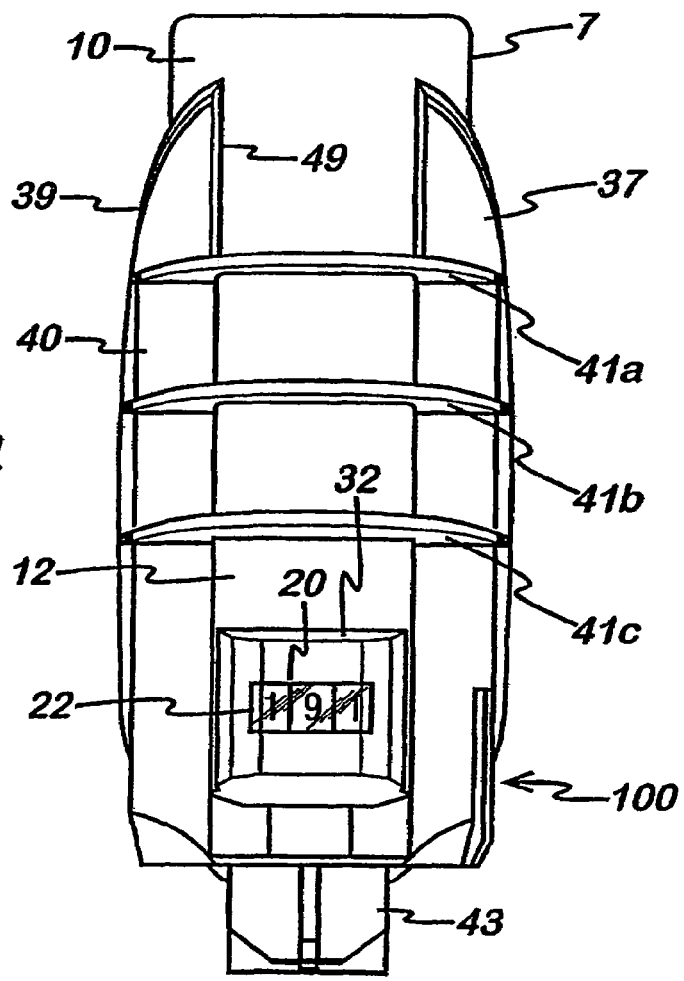
FIG. 14 is a rear view of the inner actuating part with the canister unit mounted therein.

FIGS. 11 to 13 show that the circumferential ribs 41a-c are intersected by longitudinal slots 42, 44. The longitudinal slots 42, 44 are positioned and sized so as to co-operate with the longitudinal ribs 27a, 27b on the inner surface 19 of the container member 9 of the outer casing part 3 to prevent rotation of the inner actuating part 5 in the container member 9 of the outer casing part 3.

It will further be seen that the inner actuating part 5 has a foot structure 43 which, as shown in FIG. 7, stands on a base surface 60 of the cavity 17a of the container member 9. The foot structure 43 includes a notch 45 on its forwardmost surface 47 which engages with the locking rib 21b at the lower end 25 of the cavity 17a of the container member 9. When the locking features 21a, 21b; 41a, 45 of the container member 9 and the inner actuating part 5 respectively engage with one another, the inner actuating part 5 is releasably fixed in place in the container member 9. Only when a sufficient separation force is applied is the inner actuating part 5 released from the container member 9.

The rear section 40 of the main body 37 of the inner actuating part 5 has a longitudinally extending guide slot 49. The guide slot 49 is sized to slidingly receive the protrusion 32 on the dose counter body 18. The canister unit 7 can only be inserted into the inner actuating part 5 when the protrusion 32 is aligned with the guide slot 49 in the inner actuating part 5, as shown in FIG. 6. Thus, the guide slot 49 acts as a track along which the protrusion 32 slidingly moves to insert the canister unit 7 into the inner actuating part 5 and retract it therefrom. The guide slot 49 also co-operates with the protrusion 32 to act as an anti-rotation feature which prevents rotation of the dose counter head 12 in the inner actuating part 5, as will be understood by reference to FIGS. 12 and 13.

As shown in FIG. 13, the inner actuating part 5 also has longitudinal spacers 50 arranged circumferentially about the inner surface of the cavity 38 so that the canister unit 7 is generally co-axially mounted in the inner actuating part 5.

At the base of the cavity 38 of the inner actuating part 5 there is provided a hollow support 51 (so-called "stem block") having a sleeve 52 with a bore 53 sized to receive the valve stem 16 of the canister 10. It will be appreciated that when the canister unit 7 is inserted axially into the cavity 38, the U-shaped upper section 28 of the dose counter head 12 encloses the support 51 on three sides thereof. The hollow support 51 includes a hollow extension 55 which extends outwardly at an acute angle α to the outer periphery of the sleeve 52. The extension 55 has a bore 57 which opens into the bore 53 of the sleeve 52.

The bore 57 of the extension 55 is co-axial with a longitudinal axis E-E of a nozzle 59 which extends forwardly and upwardly at an acute angle β to the outer peripheral surface of the body 37 of the inner actuating part 5. The acute angles α, β may be the same, or substantially the same. As shown in FIG. 1, the nozzle 59 is shaped and sized to be received in a nostril 94 of a nose 96 of the patient 92.

FIG. 15A shows the canister unit 7 mounted in the inner actuating part 5 with the valve stem 16 held in the bore 53 of the sleeve 52 of the hollow support 51. As will be understood by comparing FIGS. 15A and 15B, in operation the canister body 14 (and counter head 12) is depressed in the direction of arrow F relative to the inner actuating part 5 and the valve stem 16, the stem 16 being held stationary in the hollow support 51. This relative movement of the canister body 14 to the valve stem 16 causes a metered dose of the drug formulation to be discharged through the valve stem 16 into the bore 53 of the sleeve 52. The drug formulation is then channeled by the extension 55 into the nozzle 59 for delivery to the patient's nostril 94. The biasing mechanism in the valve assembly causes the canister body 14 to re-adopt the inoperative position shown in FIG. 15A on release of the depressing force F ready for the next actuation cycle.

It can therefore be seen from the above that the inner actuating part 5 contains all of the actuating elements for causing actuation of the canister 10 so that the drug formulation is discharged therefrom into the patient 92. In other words, the inner actuating part 5 is adapted to actuate the canister 10 when separate from the outer casing part 3.

Moreover, the base of the cavity 38 of the inner actuating part 5 carries a rack-like post 61 having a serrated outer profile 63 (teeth) which co-operates with the dose counter mechanism such that on depression of the canister body 14 in the inner actuating part 5 to its operative position shown in FIG. 15B, the rack-like post 61 drives a cog system in the dose counter mechanism (see WO98/56444 and PCT/EP03/06466 supra) so that the counter 22 in the display 20 is advanced to reflect that the canister 10 has been actuated to dispense a dose of the drug formulation.

It will be observed from FIGS. 11 to 13, for example, that the main body 37 of the inner actuating part 5 has an aperture 100 through a side thereof which is aligned with the rack-like post 61. The aperture 100 is left by that member of the inner actuating part mould assembly used to form the post 61. In this regard, it will be gathered from FIG. 13 that the post 61 does not register with the nozzle 59. That is to say, the post 61 is offset to the nozzle axis E-E such that it would not be possible to have the mould member for the post 61 extracted through the nozzle 59. This is because the nozzle diameter has to be small enough to be insertable into the patient's nostril 94 and the post 61 is positioned to one side of the hollow support 51 which is in registration with the nozzle 59 for fluid communication therebetween.

As will be realised, the rack-like post 61 can be replaced by any other dose counter mechanism driver structure as dictated by the form of the dose counter mechanism. Accordingly, the dose counter mechanism driver can take the form of another type of mechanical element or a non-mechanical element, for example. Again, reference may be had to WO98/56444 supra.

It can be seen from FIG. 2 that once the canister unit 7 is assembled with the inner actuating part 5 and this assembly snap-fitted into the outer casing part 3, the outer casing part 3 acts as a protective casing for the canister unit 7 when in its closed state as it prevents actuation of the canister unit 7 and shields the nozzle 59 of the inner actuating part 5.

Operation

To use the intranasal device 1, the patient 92 moves the cover member 11 of the outer casing part 3 from the closed position shown in FIG. 2 to the open position shown in FIG. 3. The cover member 11 is then pivoted to the second angular position shown in FIG. 4A and then nested with the container member 9, as shown in FIG. 4B. Then, as shown in FIG. 1, the patient 92 grips the outer casing member 3 in one hand 90 and inserts the nozzle 59 into the nostril 94. The patient 92 then actuates the device 1 by depressing the canister body 14 into the inner actuating part 5 relative to the valve stem 16 with the index finger 98. This results in a metered dose of the drug formulation being delivered to the nostril.

Actuation of the device 1 can be confirmed by the patient 92 observing whether the dose counter 22 has been advanced (decremented/incremented). The patient 92 then closes the outer casing part 3 to protect the inner actuating part 5 and canister unit 7 until the next dose is required to be dispensed.

As will be seen from FIG. 1, when the outer casing part 3 is in its open state it acts as a holder/applicator for the patient 92 in the sense that the patient 92 is able to grip the outer casing part 3 in one hand 90 and to depress the canister body 14 (and counter head 12) into the inner actuating part 5 with the index finger 98 to cause a dose of the drug formulation to be dispensed through the nozzle 59 and the counter 20 to be incremented/decremented.

One of the numerous advantages of the intranasal device 1 is the use of separable outer casing and inner actuating parts 3, 5. Recalling that the inner actuating part 5 contains all of the functional features for actuating the canister unit 7, both from a drug delivery and dose counting point of view, this is the only part which needs to be tested and submitted for regulatory approval; The outer casing part 3 does not affect the performance of the inner actuating part 5 in any way. This would be in contrast to the case where the outer and inner parts 3, 5 are integrally formed. In this instance, any change to the external shape and configuration after approval would necessitate a new application for approval since the alteration may have an adverse effect on the internal functional features, especially if the component is moulded from a plastics material.

So, the inner actuating part 5 is able to be designed first and then the decorative outer protective casing part 3 designed afterwards. In this way, the inner actuating part 5 can be tested and submitted for regulatory approval before the outer casing part 3 is finalised. This shortens the lead time for developing an approved drug delivery device. Moreover, the outer casing part 3 can be re-designed to maintain a contemporary appearance etc. without requiring a new round of regulatory tests.

Appropriate drugs (or medicaments) for use in the present invention, for instance forming part of a pharmaceutical aerosol formulation having a fluid propellant, e.g. a HFA propellant, such as HFA 134a or HFA 227, may be selected from, for example, analgesics, e.g., codeine, dihydromorphine, ergotamine, fentanyl or morphine; anginal preparations, e.g., diltiazem; antiallergics, e.g., cromoglycate (e.g. as the sodium salt), ketotifen or nedocromil (e.g. as the sodium salt); anti-infectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone (e.g. as the furoate ester), ciclesonide, triamcinolone (e.g. as the acetonide), 6α, 9α-difluoro-11β-hydroxy-16α-methyl-3-oxo-17α-propionyloxy-androsta-1,4-diene-17β-carbothioic acid S-(2-oxo-tetrahydro-furan-3-yl) ester or 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; PDE4 inhibitors e.g. cilomilast or roflumilast; leukotriene antagonists e.g. montelukast, pranlukast and zafirlukast; [adenosine 2a agonists, e.g. 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate)]; [α4 integrin inhibitors e.g. (2S)-3-[4-({[4-(aminocarbonyl)-1-piperidinyl]carbonyl}oxy)phenyl]-2-[((2S)-4-methyl-2-{[2-(2-methylphenoxy)acetyl]amino}pentanoyl)amino] propanoic acid (e.g. as free acid or potassium salt)], diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagons. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament and/or to minimise the solubility of the medicament in the propellant.

Preferably, the medicament is for the treatment of inflammatory and/or allergic conditions of the nasal passages such as rhinitis, e.g. seasonal and perennial rhinitis as well as other local inflammatory conditions such as asthma, COPD and dermatitis. Preferably, the medicament is an anti-inflammatory compound for the treatment of asthma or rhinitis.

It is to be understood that the exemplary embodiments of the present invention outlined above are for the purposes of illustration only, and that the invention can be modified, varied and take on other guises within the scope of the appended claims. Mindful of this, the use of reference numerals in the claims is not to be taken as having a limiting effect on the scope of the claims.

For the avoidance of doubt, the use herein of terms such as "generally", "substantially", "about" and the like when referring to a parameter of the invention is meant to include the absolute parameter.

The invention claimed is:

1. A hand-operated drug delivery device for delivering to a patient a drug composition from a container which contains the drug composition, the container adapted to be placed in a dispensing mode thereof on application of an actuating condition thereto which comprises movement of a first part of the container relative to a second part of the container, the device comprising:
   a dispensing unit adapted to receive the container, the dispensing unit having an actuating mechanism hand-operable to apply the actuating condition to the container and an outlet through which the drug composition is dispensable from the device, the actuating mechanism configured to hold the second part of the container stationary and to allow the first part to move relative thereto for dispensing the drug composition from the container; and
   a casing unit for the dispensing unit, the casing unit configured to be movable between a closed state in which the casing covers the outlet, and an open state in which the casing unit uncovers the outlet;
and wherein:
   the dispensing and casing units have securing features for fixedly securing the units together;
   the actuating mechanism is hand-operable to apply the actuating condition to the container when the dispensing unit is fixedly secured to the casing unit with the casing unit in the open state, but not the closed state;
   the securing features are adapted to releasably secure the casing unit and the dispensing unit together so that the casing unit is removable from the dispensing unit;
   in the closed state, the casing unit is configured to enclose the dispensing unit with the container received therein;
   the dispensing unit is hand-operable to apply the actuating condition to the container when the dispensing unit is independent from the casing unit;
   the dispensing unit is adapted to receive the container such that, when the dispensing unit is independent from the casing unit, the first part is accessible to a digit of a patient's hand to enable the digit to move the first part relative to the second part; and
   the casing unit is adapted such that when fixedly secured with the dispensing unit, and in the open state, the first part of the container is accessible to the digit of the patient's hand to enable the digit to move the first part relative to the second part and, when the casing unit is in the closed state, the first part of the container is inaccessible to the digit of the patient's hand.

2. The device of claim 1 which is hand-held.

3. The device of claim 2 in which the device is adapted to be held by the casing unit when assembled with the dispensing unit.

4. The device of claim 1 adapted so that, when the casing unit is held by a hand of a patient, the hand of the patient is also able to operate the actuating mechanism of the dispensing unit.

5. The device of claim 1 wherein the container has a plurality of doses of the drug composition and is fitted with a dose counter mechanism, and wherein the dispensing unit has a dose counter advancing mechanism adapted in use to advance the dose counter mechanism when the actuating condition is applied by the dispensing unit to the container.

6. The device of claim 5 wherein the dose counter advancing mechanism has a mechanical feature which engages the dose counter mechanism to advance it on relative movement of the first part of the container to the second part thereof.

7. The device of claim 6 in which the mechanical feature is a post.

8. The device of claim 6 in which the mechanical feature is a part of a rack-and-pinion mechanism, the other part being in the dose counter mechanism.

9. The device of claim 1 in which the outlet forms a part of a nozzle arrangement in the dispensing unit for directing the drug composition to the patient on application of the actuating condition to the container.

10. The device of claim 9 wherein, the outlet of the container is held stationary by the nozzle arrangement.

11. The device of claim 1, wherein the second part of the container presents an outlet of the container.

12. The device of claim 1, wherein the second part is a valve which is moved between a closed position and an open position on relative movement with the first part.

13. The device of claim 12, wherein the container is an aerosol container with the first part a canister.

14. The device of claim 1 further comprising the container and the drug composition therein.

15. The device of claim 14 in which the drug composition is for the treatment or prophylaxis of a respiratory disease or disorder.

16. The device of claim 1 which is an inhalation device or an intranasal device.

17. A drug delivery system comprising the device of claim 1 and at least one further dispensing unit, the dispensing units being interchangeable with one another.

18. The device of claim 1, wherein the casing unit comprises a container member which defines a cavity in which the dispensing unit is releasably, fixedly securable, and a cover member which is movably mounted on the container member for movement between closed and open positions relative to the cavity to respectively place the casing unit in the closed and open states.

19. The device of claim 18, wherein the cover member is adapted to cover the outlet of the dispensing unit in the closed position and to uncover the outlet in the open position.

20. The device of claim 1 wherein the dispensing unit is adapted to receive the container such that the first part protrudes therefrom.

21. The device of claim 1 wherein the casing and dispensing units are releasably and fixedly secured together, optionally with a container received in the dispensing unit.

22. A method of manufacturing a hand-operated drug delivery device for delivery of a drug formulated in a drug container which is adapted to be placed in a dispensing mode on application of an actuating condition thereto which comprises movement of a first part of the container relative to a second part of the container, the method comprising the steps of:
   providing a dispensing unit for receiving the container, the dispensing unit having an actuating mechanism hand-operable to apply the actuating condition to the container and an outlet through which the drug formulation is dispensed on application of the actuating condition to the container, the actuating mechanism configured to hold the second part of the container stationary and to allow the first part to move relative thereto for dispensing the drug composition from the container; and separately providing a casing unit adapted to fixedly hold the dispensing unit such that the drug is dispensable from the container by the dispensing unit when held by the casing unit, the casing unit configured to be movable between a closed state in which the casing covers the outlet, and an open state in which the casing unit uncovers the outlet;

and wherein:

the dispensing and casing units have securing features for fixedly securing the units together;

the actuating mechanism is hand-operable to apply the actuating condition to the container when the dispensing unit is fixedly secured to the casing unit with the casing unit in the open state, but not the closed state;

the securing features are adapted to releasably secure the casing unit and the dispensing unit together so that the casing unit is removable from the dispensing unit;

in the closed state the casing unit is configured to enclose the dispensing unit with the container received therein;

the dispensing unit is hand-operable to apply the actuating condition to the container when the dispensing unit is independent from the casing unit;

the dispensing unit is adapted to receive the container such that, when the dispensing unit is independent from the casing unit, the first part is accessible to a digit of a patient's hand to enable the digit to move the first part relative to the second part; and the casing unit is adapted such that when fixedly secured with the dispensing unit, and in the open state, the first part of the container is accessible to the digit of the patient's hand to enable the digit to move the first part relative to the second part and, when the casing unit is in the closed state, the first part of the container is inaccessible to the digit of the patient's hand.

23. The method of claim 22 in which the drug delivery device is hand-held.

24. The method of claim 22 in which the dispensing unit is provided with at least a part of a dose counting mechanism.

25. The method of claim 22 in which the drug container has a dose counter and the dispensing unit has a dose counter advancing mechanism for advancing the dose counter on application of the actuating condition.

26. The method of claim 25 in which the dose counter advancing mechanism is a mechanical mechanism.

27. The method of claim 26 in which the dose counter advancing mechanism is a mechanical member in the casing unit which interengages with the dose counter to advance it on application of the actuating condition.

28. The method of claim 27 in which the mechanical member is a rack member.

29. The method of claim 22 in which the dispensing unit has a valve stem support for receiving a valve stem of a valve mechanism of the container, relative movement of the container to the dispensing unit causing depression of the valve stem for release of a dose of the drug from the container.

30. The method of claim 22 in which the outlet of the dispensing unit is an exhaust duct for channeling the drug to the external environment when released from the container.

31. A drug delivery device formed by the method of claim 22.

32. A hand-operated drug delivery device for delivering to a patient a drug composition from a container which contains the drug composition, the container adapted to be placed in a dispensing mode thereof on application of an actuating condition thereto which comprises movement of a first part of the container relative to a second part of the container, the device comprising:

a dispensing unit adapted to receive the container, the dispensing unit having an actuating mechanism hand-operable to apply the actuating condition to the container and an outlet through which the drug composition is dispensable from the device, the actuating mechanism configured to hold the second part of the container stationary and to allow the first part to move relative thereto for dispensing the drug composition from the container; and a casing unit for the dispensing unit, the casing unit configured to be movable between a closed state in which the casing covers the outlet, and an open state in which the casing unit uncovers the outlet, the casing unit comprising a container member which defines a cavity in which the dispensing unit is releasably, fixedly securable, and a cover member which is movably mounted on the container member for movement between closed and open positions relative to the cavity to respectively place the casing unit in the closed and open states;

and wherein:

the dispensing and casing units have securing features for fixedly securing the units together;

the actuating mechanism is hand-operable to apply the actuating condition to the container when the dispensing unit is fixedly secured to the casing unit with the casing unit in the open state, but not the closed state;

the securing features are adapted to releasably secure the casing unit and the dispensing unit together so that the casing unit is removable from the dispensing unit;

in the closed state, the casing unit is configured to enclose the dispensing unit with the container received therein;

the dispensing unit is hand-operable to apply the actuating condition to the container when the dispensing unit is independent from the casing unit; and wherein the dispensing unit is adapted to receive the container such that, when the dispensing unit is independent from the casing unit, the first part is accessible to a digit of a patient's hand to enable the digit to move the first part relative to the second part and wherein the casing unit is adapted such that when fixedly secured with the dispensing unit, and in the open state, the first part of the container is accessible to the digit of the patient's hand to enable the digit to move the first part relative to the second part and, when the casing unit is in the closed state, the first part of the container is inaccessible to the digit of the patient's hand.

33. The device of claim 32, wherein the cover member is adapted to cover the first part of the container when in the closed position and to uncover the first part when in the open position.

34. A hand-operated drug delivery device for delivering to a patient a drug composition from a container which contains the drug composition, the device comprising:

a container that includes a drug composition therein, the container adapted to be placed in a dispensing mode thereof on application of an actuating condition thereto which comprises movement of a first part of the container relative to a second part of the container;

a dispensing unit adapted to receive the container, the dispensing unit having an actuating mechanism hand-operable to apply the actuating condition to the container and an outlet through which the drug composition is dispensable from the device, the actuating mechanism configured to hold the second part of the container stationary and to allow the first part to move relative thereto for dispensing the drug composition from the container; and a casing unit for the dispensing unit, the casing unit configured to be movable between a closed state in which the casing covers the outlet, and an open state in which the casing unit uncovers the outlet;

and wherein:

the dispensing and casing units have securing features for fixedly securing the units together;

the actuating mechanism is hand-operable to apply the actuating condition to the container when the dispensing unit is fixedly secured to the casing unit with the casing unit in the open state, but not the closed state;

the securing features are adapted to releasably secure the casing unit and the dispensing unit together so that the casing unit is removable from the dispensing unit;

in the closed state, the casing unit is configured to enclose the dispensing unit with the container received therein;

the dispensing unit is hand-operable to apply the actuating condition to the container when the dispensing unit is independent from the casing unit; and wherein the dispensing unit is adapted to receive the container such that, when the dispensing unit is independent from the casing unit, the first part is accessible to a digit of a patient's hand to enable the digit to move the first part relative to the second part and wherein the casing unit is adapted such that when fixedly secured with the dispensing unit, and in the open state, the first part of the container is accessible to the digit of the patient's hand to enable the digit to move the first part relative to the second part and, when the casing unit is in the closed state, the first part of the container is inaccessible to the digit of the patient's hand.

* * * * *